United States Patent
Dohner et al.

(10) Patent No.: US 7,169,409 B2
(45) Date of Patent: Jan. 30, 2007

(54) METHOD FOR PREVENTING CRYSTAL FORMATION IN A DISPERSION OF A LIQUID IN A MATRIX

(75) Inventors: John W. Dohner, Portola Valley, CA (US); Scott A. Bura, San Jose, CA (US)

(73) Assignee: Alza Corporation, Mountain View, CA (US)

( * ) Notice: Subject to any disclaimer, the term of this patent is extended or adjusted under 35 U.S.C. 154(b) by 39 days.

(21) Appl. No.: 10/658,247

(22) Filed: Sep. 8, 2003

(65) Prior Publication Data

US 2004/0047893 A1    Mar. 11, 2004

Related U.S. Application Data

(63) Continuation of application No. 09/144,718, filed on Sep. 1, 1998, now abandoned, which is a continuation of application No. 08/951,943, filed on Oct. 17, 1997, now Pat. No. 6,569,448, which is a continuation of application No. 08/566,228, filed on Dec. 1, 1995, now abandoned.

(51) Int. Cl.
 *A61K 9/70* (2006.01)
(52) U.S. Cl. ..................... 424/448; 424/449
(58) Field of Classification Search ............... 424/448, 424/449
See application file for complete search history.

(56) References Cited

U.S. PATENT DOCUMENTS

| | | | |
|---|---|---|---|
| 3,598,122 A | 8/1971 | Zaffaroni |
| 3,598,123 A | 8/1971 | Zaffaroni |
| 3,797,494 A | 3/1974 | Zaffaroni |
| 4,031,894 A | 6/1977 | Urquhart et al. |
| 4,060,084 A | 11/1977 | Chandrasekaran et al. |
| 4,144,317 A | 3/1979 | Higuchi et al. |
| 4,201,211 A | 5/1980 | Chandrasekaran et al. |
| 4,262,003 A | 4/1981 | Urquhart et al. |
| 4,308,621 A | 12/1981 | Mendelson |
| 4,379,454 A | 4/1983 | Campbell et al. |
| 4,436,741 A | 3/1984 | Urquhart et al. |
| 4,832,953 A | 5/1989 | Campbell et al. |
| 5,370,924 A | 12/1994 | Kochinke |
| 5,662,928 A * | 9/1997 | Braun .................. 424/449 |

FOREIGN PATENT DOCUMENTS

| | | |
|---|---|---|
| DE | 42 23 360 | 4/1993 |
| EP | 0 304 227 B1 | 3/1993 |

OTHER PUBLICATIONS

International Search Report For Corresponding PCT Application No. PCT/US96/18397.

* cited by examiner

*Primary Examiner*—Thurman K. Page
*Assistant Examiner*—Sharon Howard

(57) ABSTRACT

An improved method for the manufacture of transdermal drug delivery devices comprising liquid dispersions of a liquid in an aqueous or nonaqueous matrix is disclosed. More particularly, the invention relates to preventing the formation of a crystalline structure in such liquid dispersions by annealing films and laminates in-line immediately following film formation and/or lamination during the manufacture of these devices.

12 Claims, 2 Drawing Sheets

METHOD FOR PREVENTING CRYSTAL FORMATION IN A DISPERSION OF A LIQUID IN A MATRIX

This application is a continuation of U.S. application Ser. No. 09/144,718, filed Sep. 1, 1998, now abandoned, which is a continuation of U.S. application Ser. No. 08/951,943, filed Oct. 17, 1997 now U.S. Pat. No. 6,569,448, which is a continuation of U.S. application Ser. No. 08/566,228, filed Dec. 1, 1995, abandoned.

FIELD OF THE INVENTION

This invention relates to the manufacture of dispersions of a liquid in an aqueous or non-aqueous matrix and to drug delivery devices which utilize these liquid dispersions. More particularly, the invention relates to preventing the formation and/or growth of a crystalline structure in films or laminates comprising such liquid dispersions by annealing the films and/or laminates immediately following film formation and/or lamination. The crystal-free films and laminates may then be formed into various articles, such as drug delivery devices.

BACKGROUND OF THE INVENTION

As used herein, "annealing" refers to a process of subjecting the liquid dispersion or article formed therefrom to a specified, elevated temperature for a predetermined minimum period of time and then allowing the dispersion or article to cool to ambient conditions.

Transdermal delivery devices comprising a dispersion of a drug or other biological agent in various aqueous or non-aqueous matrices are known in the art as described in U.S. Pat. Nos. 3,598,122, 3,598,123, 4,031,894, 4,144,317, 4,201,211, 4,262,003, 4,379,454, and 4,436,741, all of which are incorporated herein in their entirety by reference. As disclosed in these patents, aqueous matrices typically comprise water or water/ethanol and 1–5 wt. % of a gelling agent such as hydroxyethylcellulose. Non-aqueous matrices are typically comprised of a polymeric material such as copolymers of ethylene vinyl acetate or blends of low molecular weight and high molecular weight polyisobutene. The drug may be in solid form or in the form of a liquid dispersion. This invention relates to such liquid drug dispersions.

In addition to the above mentioned patents, U.S. Pat. No. 5,370,924, incorporated herein in its entirety by reference, discloses methods for manufacturing transdermal drug delivery devices. The methods disclosed in this patent describe a process whereby the various elements of a transdermal device may be fabricated separately and joined together in a final manufacturing step.

Although this invention will be described hereafter specifically with respect to scopolamine delivery devices, it should be recognized that it is applicable to dispersions of any other drug or biological agent in matrices where a crystalline structure may be formed. Such drugs or agents such as nicotine, secoverine, and benztropine, for example, may, to the extent they form crystalline structures, be treated in a manner similar to the methods by which dispersions of scopolamine base are treated according to this invention.

Transdermal delivery devices for the administration of scopolamine of the type disclosed in U.S. Pat. No. 4,031,894 cited above are used extensively for the prevention of motion sickness. The original manufacture of the product is described in the patent by solvent casting of chloroform solutions of scopolamine base in polyisobutene (PIB) and mineral oil (MO) onto impermeable webs to form drug reservoir and contact adhesive films. Upon evaporation of the chloroform, a dispersion of liquid scopolamine base in the PIBIMO matrix is formed. The drug reservoir and contact adhesive films are then laminated to opposite sides of a release rate controlling membrane, formed from a mineral oil impregnated microporous film, to produce a final laminate comprising a removable release liner layer, an adhesive layer, a rate controlling membrane layer, a drug reservoir layer, and an impermeable backing lamina. The final laminate is then die cut into individual systems and packaged in individual heat sealed pouches.

The manufacture of the product in this manner was carried out for approximately five years without any indication of the formation of crystals in either the drug reservoir or the adhesive. After that time, small crystals of scopolamine hydrate were observed infrequently but this did not present a problem because the release rate of the drug from the device was not affected by the presence of the small number of small crystals then occurring. In addition to the small number and size of the crystals, another reason that the release rates were not affected is attributed to the observation that the crystal size did not change appreciably (i.e. minimal if any crystal growth) with time in the pouch.

Approximately two years later, larger numbers of rapidly propagating crystals were observed in the drug reservoir, with a lower incidence observed in the contact adhesive layer which contained a lower concentration of scopolamine base. At that time, the size of the crystals and their frequency of occurrence had increased to the point where they produced a significant adverse effect on the release rate of scopolamine from the device. Thereafter, every lot manufactured developed unacceptably high crystal size and frequency and commercial production had to be halted until the problem could be solved.

Crystallization was most noticeable after the step in which the final laminate film was cut into individual devices. After the final laminate film was fed through the die-cutting machine for the formation of individual transdermal delivery units, crystallization began around the edges of the cut product and crystalline growth thereafter propagated rapidly throughout the mass of the reservoir and in some cases the adhesive layer. Visually observable crystals were not necessarily apparent immediately after the cutting step; instead they would typically develop over a period of days. These crystals were identified as a hydrate form of scopolamine base.

Various attempts to eliminate the problem were tried over the next several months, all to no avail. For example, the drug reservoir film, adhesive film, and the final laminate film were heated overnight, yet crystallization after die-cutting still occurred. Similarly, the casting solutions were heated and allowed to stand for extended periods also with no effect. Attempts to reduce the amount of residual water in the chloroform solution of the scopolamine base by drying with extra amounts of drying agents such as anhydrous sodium sulfate and magnesium sulfate were also unsuccessful as crystallization still occurred. Extensive cleaning of contacting surfaces reduced but did not eliminate the presence of crystals after die-cutting.

A successful process for the prevention of the formation of the scopolamine hydrate crystals was ultimately discovered and is described in U.S. Pat. No. 4,832,953, incorporated in its entirety herein by reference. According to that invention, formation of crystalline hydrates in a liquid dispersion of a hydratable liquid in a non-aqueous, typically polymeric, matrix can be prevented if, after they have been placed in their packages, the articles are heated to a temperature above the melting point of the crystalline hydrate, are maintained at that temperature for a period of time, and then are allowed to cool to ambient conditions. For this process to be successful, holding times for cast films and laminates, prior to die-cutting, pouching, and annealing, were minimized in an effort to outrace the kinetics of crystal growth. It was found that when so treated, crystals initially present disappeared, did not reform upon cooling to ambient conditions, and there were no additional signs of crystal formation or growth after storage at ambient conditions and under accelerated aging conditions for several months.

The commercial manufacture of the product including the step of annealing the pouched systems as described in U.S. Pat. No. 4,832,953 was then-carried out for approximately seven years before the current crystallization problem developed and commercial production again had to be halted. The measures employed to prevent formation of the hydrate as taught in the U.S. Pat. No. 4,832,953 are not effective in preventing the formation of the newly observed crystals because: 1) the new crystals do not melt at the annealing temperatures specified therein; and 2) the kinetics of the new crystal growth are significantly faster, such that films cannot practically be moved through the manufacturing process fast enough to eliminate significant crystal growth. Crystals have been observed only four hours after film casting and have been observed in the final product.

An extensive investigation was undertaken, including examination of raw materials, process equipment, and procedures to isolate a source of crystallization, during which it was determined that crystal formation could not be attributed to any specific feature of the procedures, equipment, or raw materials used to produce the product. It was confirmed that rapid crystallization could start after any manufacturing step involving the scopolamine films and laminates. Production was halted until the problem was solved according to this invention.

SUMMARY OF THE INVENTION

The new crystal has been identified as a crystalline form of anhydrous scopolamine base. The cause of the change from the previous hydrate form to a more stable anhydrous crystal form is unknown. The inventors have found that the annealing of all the individual scopolamine-containing films and laminates, in addition to the final laminate and pouched system, successfully prevents the formation and growth of the currently observed scopolamine crystalline structure. The invention provides a method to effectively beat the crystal growth kinetics in a practical manner.

It is accordingly an aspect of this invention to prevent the formation and/or growth of a crystalline structure in a dispersion of a liquid in an aqueous or non-aqueous matrix.

It is another aspect of this invention to prevent the formation and/or growth of a crystalline structure of scopolamine in dispersions of scopolamine base in a non-aqueous matrix.

It is another aspect of this invention to manufacture transdermal therapeutic systems for the controlled delivery of scopolamine base which are free from crystals of scopolamine.

It is yet another aspect of this invention to provide an improved method of manufacture of transdermal therapeutic systems which prevents the formation and/or growth of a crystalline structure in dispersions of a liquid in an aqueous or nonaqueous matrix.

These and other aspects of this invention will be readily apparent from the following description of the invention.

DISCLOSURE OF THE INVENTION

Figure 1:
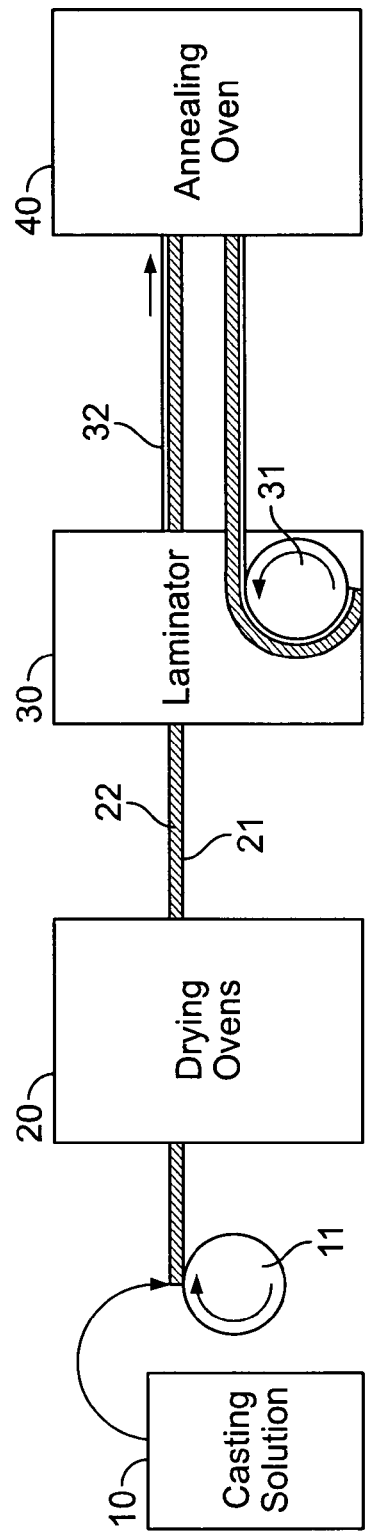
FIG. 1 is a flow diagram depicting the process of forming the drug reservoir/backing layer according to a preferred embodiment of this invention.

According to this invention, formation and/or growth of a crystalline structure in a dispersion of a liquid in an aqueous or non-aqueous matrix can be prevented if, immediately following the formation of each and every film or laminate of the dispersion, the layer(s) containing the liquid dispersion is (are) sandwiched between non-porous films and subjected to an annealing process wherein they are heated to a sufficient temperature for a sufficient time and then allowed to cool. Preferably, the following conditions are satisfied at each annealing step: 1) the melting point temperature of the crystal is exceeded; 2) sufficient time is provided to allow the crystal to melt; 3) the dispersion is protected from environmental exposure until the next manufacturing (and annealing) step; and 4) the annealing step begins promptly after film formation and/or lamination. Films and laminates treated by this annealing process are stable and have been observed to remain crystal-free after storage at ambient conditions for at least 90 days.

A preferred embodiment of this invention is directed to the manufacture of transdermal delivery devices. It has been found that transdermal delivery devices manufactured according to this invention are free from crystals and exhibit release rates within applicable specifications for the product. Although this invention will be described with respect to a specific example relating to the manufacture of transdermal delivery devices for the controlled delivery of scopolamine, it should be recognized that this invention is applicable to the processing of dispersions of any liquid agent capable of forming a crystalline structure.

According to this preferred embodiment, individual films and laminates of a transdermal therapeutic system which comprise a dispersion of a liquid in a matrix, as well as the final laminate and pouched system, are subjected to an annealing process immediately following the formation of the films or laminates. The annealing process is performed immediately after the film is placed between two non-porous substrates in order to minimize exposure of the film to the atmosphere. The film or laminate thus treated is stable with respect to crystal growth until the next processing step, assuming exposure of the annealed film to the environment is controlled.

In a particularly preferred embodiment directed to the manufacture of transdermal delivery devices containing scopolamine, the rate control membrane/contact adhesive films, drug reservoir films, and final laminate films are protected between two non-porous substrates and are subjected to an annealing process, immediately following lamination, and are heated to a sufficient temperature, for a sufficient time, and then allowed to cool to ambient conditions in order to prevent subsequent crystal formation and growth. The final laminate is then cut into individual systems, placed into sealed containers, and then subjected to an additional annealing step.

The formation of the films and laminates may be achieved by any means known in the art. Although this invention will be described with respect to an example wherein a solvent casting procedure is utilized to form the various films, it should be recognized that other procedures for forming the films, such as extrusion or reverse roll coating, may be used in the practice of this invention. For example, if an extrusion process is used to form the various films, it would not be necessary to use the drying ovens in the manufacturing processing line and the extruded films would proceed directly to the annealing oven or to a lamination stage immediately followed by the annealing step of this invention.

The annealing of the films and laminates can be achieved by various means. For example, when the films are formed by solvent casting, annealing can be performed by a second pass through the drying ovens that are used to dry the initial film. This requires that by the time the last portion of film has exited the ovens for the first time the portion of film that first exited the ovens has not already begun to crystallize. Alteratively, the film casting may be broken up into small sublots so that any film or laminate is subjected to annealing within a few hours of casting or lamination. Preferably, annealing occurs in-line, immediately following film formation and/or lamination. Most preferably, an annealing oven is placed immediately after the lamination stage.

The manufacture of transdermal delivery devices using a solvent casting procedure will now be described with reference to the drawings. The process for the formation of the drug reservoir layer is shown in FIG. 1. The drug reservoir casting solution is cast onto impermeable backing layer 21 fed from source roll 11 to form a film comprising drug reservoir layer 22 on impermeable backing layer 21. The film is then passed through the drying ovens 20 to evaporate the solvent. The dried film is then passed through a laminator 30 where non-porous interleaving layer 32 is applied to the surface of drug reservoir layer 22. The laminate is then passed through in-line annealing oven 40, shown in detail in FIG. 4. After exiting the annealing oven, the laminate is wound up on take-up roll 31 of the laminator.

Figure 2:
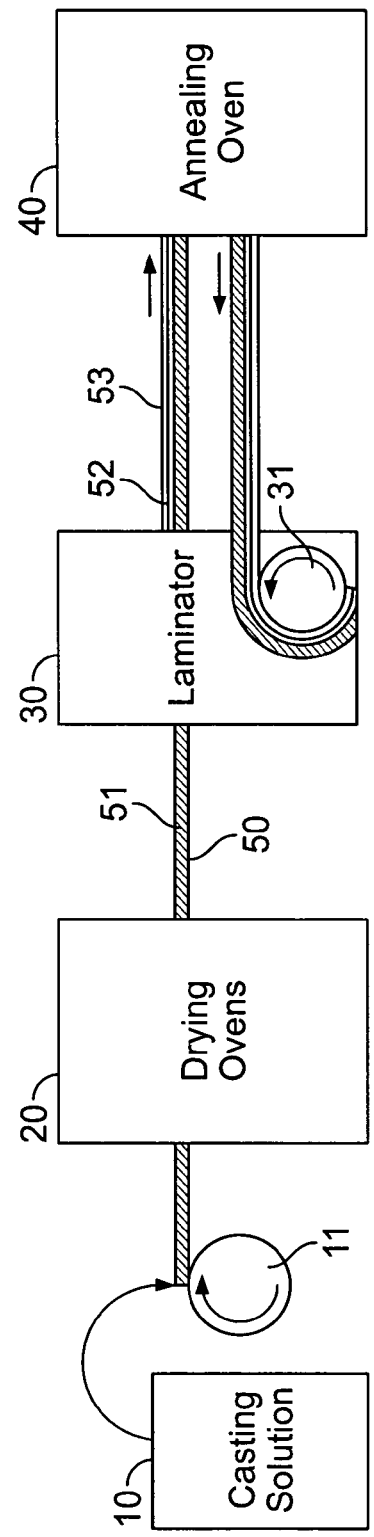
FIG. 2 is a flow diagram depicting the process of forming the rate control membrane/contact adhesive layer according to a preferred embodiment of this invention.

The rate control membrane/contact adhesive layer is formed by a similar process as shown in FIG. 2. The contact adhesive solution 51 is cast onto release liner 50 and passed through the drying ovens 20. Rate control membrane 52 and non-porous interleaving layer 53 are then laminated to the surfaces of the contact adhesive and rate control membrane, respectively. The laminate is then passed through the in-line annealing oven 40 before being taken up on the take-up roll 31 of the laminator.

Figure 3:
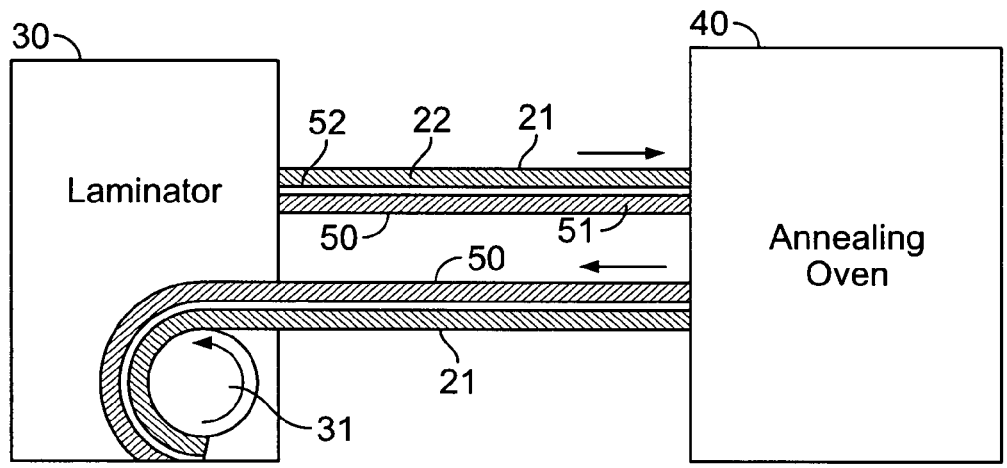
FIG. 3 is a flow diagram depicting the process of forming the final laminate according to a preferred embodiment of this invention.

The final laminate is produced as shown in FIG. 3. The drug reservoir laminate and rate control membrane/contact adhesive laminate rolls are set up in the laminator. Interleaving layer 53 is removed from the rate control membrane/contact adhesive laminate and interleaving layer 32 is removed from the drug reservoir laminate, exposing the rate control membrane 52 and drug reservoir 22, respectively, which are then laminated together to form the final laminate. The final laminate, comprising impermeable release liner 50, contact adhesive layer 51, rate control membrane 52, drug reservoir layer 22, and impermeable backing layer 21, is then passed through in-line annealing oven 40 before being taken up once again on take-up roll 31 of the laminator. In a final processing step (not shown), individual systems are die cut from the final laminate. The systems are placed in individual pouches, the pouches are heat sealed and the pouched systems are then placed in an in-line annealing oven for a final annealing process.

Figure 4:
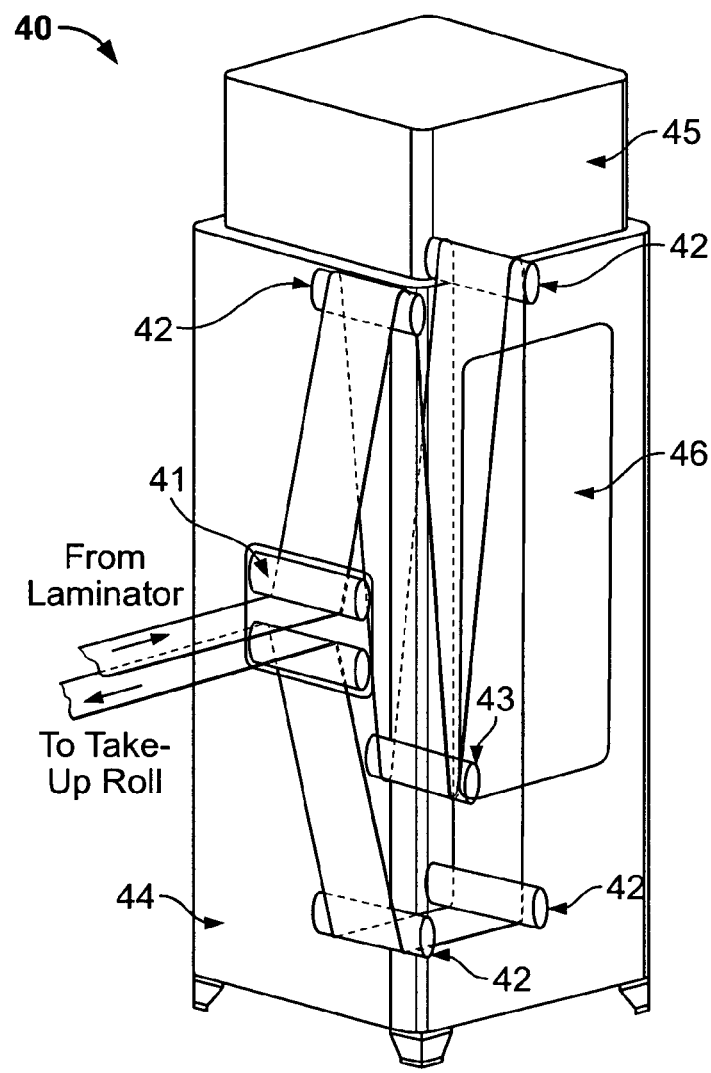
FIG. 4 is an isometric view of an in-line annealing oven useful for the purposes of the present invention.

FIG. 4 depicts annealing oven 40 in greater detail. The laminate first enters the annealing oven where it contacts heated roll 41 which provides immediate heating to the laminate. The laminate passes over idler rolls 42 and tension roll 43 and is passed through the annealing chamber 44 which is preheated to a predetermined temperature. The dwelling time of the laminate in the annealing chamber may be adjusted by setting an appropriate line speed for the laminate. Annealing oven 40 is also provided with air handler 45 and access door 46.

As seen in the above description, at each film forming/laminating step, the adhesive is sandwiched between non-porous substrates so that after annealing is performed, additional contamination by crystal seeds is not possible until the next processing operation. After each intermediate film or laminate is annealed, that product is stable until the next operation, as long as it is not exposed to the atmosphere.

The use of an in-line annealing oven offers several advantages to alternative methods of annealing individual films and laminates. First, it eliminates the need for breaking the production down into small sublots in order to reduce film exposure time, thus allowing for production at the previous full lot capacity. Such a method also reduces the film exposure time more effectively to only a matter of seconds. Additionally, the use of an in-line annealing oven allows for better utilization of the casting ovens and avoids the difficulty in handling the laminates as would be required if they were to be run through the casting ovens a second time. With the in-line annealing method of this invention, better prevention of crystal formation is observed because only seconds elapse between the time that the film leaves the casting ovens and enters the annealing oven, effectively beating crystal growth kinetics by eliminating any time available for crystal formation and/or growth.

The temperature and time are not critical provided they are adequate to prevent the formation of crystals after cooling and are not so high as to cause damage to the individual films or laminas. If crystals are initially present, the temperature must be at, and preferably above, the melting point of the crystal and the time should be sufficient to cause melting of all the crystals present. If crystals are not present at the time of the heating step, temperatures lower than the melting point of the crystal may be effective. Nevertheless, it is preferable from the point of quality assurance and uniformity of processing conditions to heat above the melting point of the crystal, the formation of which it is desired to prevent.

In the preferred embodiment of this invention directed to the prevention of the formation of scopolamine crystals during the manufacture of transdermal therapeutic systems containing scopolamine, the temperature to which the individual and final laminates were heated is preferably within the range of 75–90° C., for a duration of 2–10 minutes. The final pouched systems are preferably heated to a temperature of 75° C. for a period of 4–24 hours. The actual temperature for other materials is easily determined by measuring the melting point of the crystal.

Having thus generally described our invention, the following specific example is provided to illustrate the invention. The example is not intended to limit the scope of the invention in any way. Unless otherwise indicated, parts are by weight.

EXAMPLE 1

Preparation of Scopolamine Base Solution

Scopolamine base was formed by dissolving scopolamine hydrobromide in an aqueous sodium bicarbonate-sodium carbonate buffer solution. Sodium hydroxide was added until a pH of about 9.6 was reached at which point the scopolamine base precipitated from solution and was extracted with chloroform.

Preparation of Casting Solutions 20.0 parts high molecular weight PIB (Vistanex L-100, 1,200,000 viscosity average molecular weight), 26.1 parts low molecular weight PIB (Vistanex LM-MS, 35,000 viscosity average molecular weight), 41.7 parts mineral oil (10 cp at 25° C.) and 11.3 parts of scopolamine base were dissolved in chloroform in a mixer to prepare the drug reservoir casting solution used in forming the drug reservoir film.

To prepare the contact adhesive casting solution, a solution of 23.1 parts of said high molecular weight PIB, 28.8 parts of said low molecular weight PIB, 46.1 parts of said mineral oil, and 2.0 parts of said scopolamine base were dissolved in chloroform in a mixer.

Preparation of Films and Laminates

The drug reservoir casting solution was then solvent cast to form a drug reservoir film approximately 50 micrometers dry thickness on an approximately 65 micrometer backing of aluminized polyethylene terephthalate (Scotchpak®). The drug reservoir film was passed through an oven to evaporate the chloroform, leaving behind a drug containing adhesive film on a backing substrate. After leaving the oven, the film was moved to a laminator where an interleaving film was applied. The laminate was then passed into a second oven placed immediately following the laminator, where the laminate was heated to a temperature of 80–85° C. for 9–10 minutes. Thereafter, the laminate is returned to the take-up roll on the laminator.

The rate control membrane/contact adhesive laminate was similarly prepared by solvent casting a 50 micrometer dry thickness adhesive layer of the contact adhesive casting solution onto a 75 micrometer siliconized, polyethylene terephthalate film. After casting, the films were passed through the ovens to evaporate the chloroform solvent, leaving behind a drug containing adhesive on a release liner. This film was moved to a laminator, where a microporous polypropylene rate controlling membrane, with the pores saturated with mineral oil, was laminated to the adhesive surface. An interleaving film was added to protect the top of the control membrane and the entire laminate was introduced into the second oven immediately thereafter and was heated to a temperature of 80–85° C. for 5–6 minutes.

The rate control membrane surface of the rate control membrane/contact adhesive laminate was then laminated to the drug reservoir surface of the drug reservoir laminate to yield a final laminate. This final laminate was then also passed through the annealing oven immediately following the laminator and heated to a temperature of 80–85° C. for approximately 2 minutes. 2.5 cm² circular disk-shaped systems were punch-cut from the resulting five layer laminate. The individual systems were then packaged within heat-sealed foil-lined pouches. The pouches were then treated by heating in an additional annealing oven to 75° C. for 4–24 hours and thereafter allowed to cool to ambient conditions.

None of the systems made according to the invention were observed to contain crystals. Additionally, systems made according to the invention exhibited release rates within the applicable specifications for the product.

Having thus described our invention, it is readily apparent that various modifications can be made by workers skilled in the art without departing from the scope of this invention. It is intended that the invention embrace these equivalents within the scope of the claims that follow.

We claim:

1. A process for the production of a scopolamine free base containing transdermal system substantially free of crystals of scopolamine free base, comprising annealing scopolamine free base containing layers of said transdermal system at a temperature above the melting point of the crystals for a period of time sufficient to melt scopolamine free base anhydrous crystals, wherein the annealing process is performed after casting a scopolamine free base containing formulation onto a web or after forming a laminate with a scopolamine free base containing formulation for use in constructing said transdermal system substantially free of scopolamine free base anhydrous crystals.

2. The process of claim 1, wherein said transdermal system is further packaged and further heat treated at a temperature of at least 67° C. to about 90° C. for a period of about 4 hours to about 24 hours.

3. The process of claim 1 wherein said annealing takes place at about 75° C. to about 90° C.

4. The process of claim 1, wherein said annealing takes place over a period of about 2–10 minutes.

5. The process of claim 1, wherein a drug reservoir layer containing scopolamine free base and a contract adhesive layer containing scopolamine free base are each separately annealed, then contacted and further annealed prior to packaging.

6. A method for manufacturing delivery devices for the transdermal administration of scopolamine comprising, in combination:
   a. forming a laminate, at lease one lamina of which comprises a dispersion of said scopolamine in a non-aqueous matrix;
   b. cutting subunits forming said delivery devices from said laminate;
   c. packaging said delivery devices in sealed containers;
   d. heating said delivery devices in said containers to a temperature above the melting point of anhydrous crystalline scopolamine and maintaining said delivery devices at such temperature for a time sufficient to prevent the formation or eliminate the presence of anhydrous crystals of scopolamine for a substantial period of time after cooling of the subunits to ambient temperatures; and
   e. cooling the delivery devices to ambient temperatures;
wherein the heating comprising heating at least each scopolamine containing layer to a temperature exceeding the melting point of scopolamine anhydrous crystal for a period of time sufficient to melt the crystals, the heating step being conducted prior to or during the process, of laminating and/or sealing the scopolamine containing layer.

7. A process for the production of a scopolamine free base containing transdermal system substantially free of anhydrous crystals of scopolamine free base, comprising annealing scopolamine free base containing layers of said transdermal system at a temperature above the melting point of the anhydrous crystals for a period of time sufficient to melt the crystals, wherein the annealing process is performed within a period after casting a scopolamine free base containing formulation onto a web for use in constructing said transdermal system so as to result in a transdermal system substantially free of anhydrous scopolamine crystals, wherein said annealing takes place at about 75° C. to about 90° C.

8. The process of claim 1, wherein the heating and annealing process is done immediately after casting a scopolamine free base containing formulation onto a web or immediately after forming a laminate with a scopolamine free base containing formulation.

9. The process of claim 1, further comprising annealing the transdermal system at a temperature above the melting point of scopolamine after packaging in pouch.

10. The process of claim 1, further comprising annealing a laminate that includes a scopolamine free base containing layer laminated to a nonporous non-scopolamine-containing layer.

11. The process of claim 10, further comprising removing the nonporous non-scopolamine-containing layer before packaging the transdermal system in pouch.

12. The process of claim 1, comprising two heating and annealing steps, one heating step being immediately after casting the scopolamine free base containing formulation onto a web.

\* \* \* \* \*